United States Patent
Bresina et al.

(10) Patent No.: US 9,655,725 B2
(45) Date of Patent: May 23, 2017

(54) WEAR-REDUCING RING FOR ARTICULATIONS IN TOTAL JOINT REPLACEMENTS

(75) Inventors: Stephen J. Bresina, Davos Dorf (CH); Slobodan Tepic, Zurich (CH)

(73) Assignee: Scyon Orthopaedics AG, Zurich (CH)

( * ) Notice: Subject to any disclaimer, the term of this patent is extended or adjusted under 35 U.S.C. 154(b) by 39 days.

(21) Appl. No.: 14/240,231

(22) PCT Filed: Aug. 31, 2012

(86) PCT No.: PCT/IB2012/001974
§ 371 (c)(1),
(2), (4) Date: Oct. 7, 2014

(87) PCT Pub. No.: WO2013/030668
PCT Pub. Date: Mar. 7, 2013

(65) Prior Publication Data
US 2015/0051707 A1    Feb. 19, 2015

Related U.S. Application Data

(60) Provisional application No. 61/529,977, filed on Sep. 1, 2011.

(51) Int. Cl.
*A61F 2/32* (2006.01)
*A61F 2/34* (2006.01)
*A61F 2/30* (2006.01)

(52) U.S. Cl.
CPC .......... *A61F 2/34* (2013.01); *A61F 2/30767* (2013.01); *A61F 2002/302* (2013.01);
(Continued)

(58) Field of Classification Search
CPC .............. A61F 2/34; A61F 2002/30016; A61F 2002/302; A61F 2002/30673;
(Continued)

(56) References Cited

U.S. PATENT DOCUMENTS

| | | | | |
|---|---|---|---|---|
| 5,019,105 A | * | 5/1991 | Wiley | A61F 2/34 623/22.29 |
| 5,181,926 A | * | 1/1993 | Koch | A61F 2/30 623/22.14 |

(Continued)

FOREIGN PATENT DOCUMENTS

| | | |
|---|---|---|
| EP | 0707838 | 4/1996 |
| EP | 1321113 | 6/2003 |
| WO | WO 2008/015288 | 2/2008 |

*Primary Examiner* — Brian Dukert
(74) *Attorney, Agent, or Firm* — Occhiuti & Rohlicek LLP (57) ABSTRACT

The articulating joint prostheses of the invention demonstrate reduced wear and can include a cup (101) formed of UHMWPE. An insert (150) of a hard material, such as metal, ceramic or cross-linked UHMWPE is positioned within the cup at a location of the contact between the cup and head (102). The shape of either component of the kinematic pair may be modified so as to result in an annular surface contact between the two components, with the insert positioned at the annular surface contact. Fluid trapped between the two components within the inner contour of the annular contact area is pressurized under load due to elastic deformation of the components and exuded out through an inter-articular gap over the surface of contact of the insert. This aids lubrication and reduces wear.

18 Claims, 10 Drawing Sheets

(52) U.S. Cl.
CPC ............... *A61F 2002/30016* (2013.01); *A61F 2002/30026* (2013.01); *A61F 2002/30031* (2013.01); *A61F 2002/3082* (2013.01); *A61F 2002/30327* (2013.01); *A61F 2002/30673* (2013.01); *A61F 2002/30685* (2013.01); *A61F 2002/30733* (2013.01); *A61F 2002/30838* (2013.01); *A61F 2002/30934* (2013.01); *A61F 2002/3241* (2013.01); *A61F 2002/3429* (2013.01); *A61F 2210/00* (2013.01)

(58) Field of Classification Search
CPC .. A61F 2002/30685; A61F 2002/30733; A61F 2002/3082; A61F 2002/30838; A61F 2002/30934; A61F 2002/30935; A61F 2002/3429
See application file for complete search history.

(56) References Cited

U.S. PATENT DOCUMENTS

| | | | | |
|---|---|---|---|---|
| 5,549,693 A * | 8/1996 | Roux | ................... | A61L 27/105 623/22.14 |
| 5,549,700 A * | 8/1996 | Graham | ................... | A61F 2/34 403/133 |
| 2005/0049716 A1 * | 3/2005 | Wagener | ............ | A61F 2/30767 623/23.5 |

* cited by examiner

Prior Art

WEAR-REDUCING RING FOR ARTICULATIONS IN TOTAL JOINT REPLACEMENTS

CROSS REFERENCE TO RELATED APPLICATIONS

This application is a U.S. national phase application of the international application PCT/IB2012/001974, filed Aug. 31, 2012, which claims the benefit of the filing date of U.S. Provisional Application No. 61/529,977, filed Sep. 1, 2011. The content of the earlier-filed application is hereby incorporated by reference herein in its entirety.

FIELD OF THE INVENTION

This invention relates to compositions and methods for reducing wear in total joint replacements. More particularly, it relates to a hardened insert within an artificial joint positioned at the location of most wear.

BACKGROUND

Ultra High Molecular Weight Polyethylene (UHMWPE) is a commonly used articulation material, and wear of this material is considered a major factor that contributes to the aseptic loosening that limits the duration of artificial joints. Reducing UHMWPE wear has been an important topic of research and development since the sixties, and investigators have worked with increasing urgency on this problem for about the last decade.

Since its introduction into total joint replacement by Charnley, UHMWPE remains the most commonly used material for the concave part of artificial joints (e.g., for the acetabular cup of the total hip prosthesis, or the tibial plateau of the total knee prosthesis). While it has played a central role in the success and widespread use of joint replacements, UHMWPE has also been identified as a major culprit in the most common mode of their failure—the aseptic loosening mentioned above. Wear particles produced by articulation of the hard, convex, usually metallic, or ceramic component against the soft polymer liner accumulate in and around the joint until the concentration of particles becomes so high that, in spite of the polymer's generally excellent biocompatibility they initiate a biological response leading ultimately to bone loss, loosening of the joint components, and dysfunction of the joint replacement.

Different methods of wear reduction have been sought, found, and introduced into clinical use over the last few decades. These methods were focused on improving the wear characteristics of the articulation pair at their interface.

When directed to the convex, metallic, or ceramic component, these wear-reduction efforts aimed to reduce roughness of the surface, increase the precision of the geometry (e.g., by improving the sphericity of the femoral head), and increase the hardness of the materials. Improved wetting of the hard surface has also been identified as an important factor in general wear reduction.

These measures have been realized through: (i) better selection and processing of metals, both in metallurgical aspects and in the machining methods employed; (ii) use of hard coatings, which can be added or created in situ (e.g., by oxidation); and (iii) use of bulk ceramic components.

The reduction of wear, both in laboratory testing and based on in vivo observations, is on the order of about a factor of two.

More recently, modifying UHMWPE material by cross-linking has attracted attention. Cross-linking can be achieved by physical means (e.g., irradiation) or chemical means. The results of laboratory testing have varied in part due to the different methods used to produce wear and the methods of assessing the resulting wear. Tests conducted on joint simulators and with careful compensation for artifacts, suggest a five- to ten-fold reduction of wear when cross-linked UHMWPE, is compared to "regular" UHMWPE.

However, there are a number of potential problems with cross-linking. These include a reduction of strength, particularly in fatigue; a reduction of average particle size, which makes the wear debris more biologically active; and risk of long term degradation in the body.

Some would argue that cross-linked UHMWPE has not been in broad clinical use for long enough to reach a conclusion on its benefit-to-risk ratio. Several clinical observations suggest the actual wear reduction has been reduced by about a factor of two but, again, there is much variability in methods used to assess the wear and thus in the reported results.

Metal-metal articulations were used before UHMWPE was introduced. As the biological problems with wear of UHMWPE surfaced in the eighties, metal-metal articulations were re-introduced, and those supported by better metallurgical and manufacturing technologies consequently promised better clinical outcomes. The wear rates, compared to UHMWPE, are lower by about a factor of ten by weight and by about a hundred times by volume. However, systemic accumulation of ions of potentially harmful metals has been observed, and the risks of this accumulation remains unknown, especially in younger patients, who are most in need of improved joint replacements.

Ceramic-ceramic articulations are technically the best in terms of wear, but various regulatory obstacles and high prices have, until recently, limited their use. There is also a risk, albeit low, that ceramic components, which are brittle, can break. Any damage to a surface or miniscule imperfections can cause rapid degradation of the articulation. Sophisticated technologies and quality controls required in production have also been an impediment to the wider use of ceramics.

Swiss patent CH449173, entitled "Gelenkprothese," by Maurice Mueller, discloses a metal on metal prosthesis, whereby the contact is limited to polymeric pads seated into recesses within the cup.

German patent DE4423020, entitled "Gelenkprothese," by Wolfgang Fitz, discloses a hip prosthesis cup with a reservoir for lubricating fluid in the unloaded, inferior region, combined with grooves, which are known in the general art of sliding bearings as advantageous because wear particles are more readily removed from the articulation.

German patent DE19604458, entitled "Gelenkpfanne," by Hagen Seifert, discloses a hip prosthesis having a cup shaped so as to make exclusively a ring contact to the head near the equator, leaving a spherically shaped recess in the cup filled with fluid. The fluid-filled recess is enabled by grooves in the contact area to act as a shock absorber. To control the stiffness of the cup, there are a number of ring-shaped cavities within the cup wall. The concept is essentially one of a hydrodynamic bearing. Devoid of fluid support, as would happen in any case because the loading must persist for just fractions of a second, the prosthesis would either experience very high friction torque (where the load is supported by the near-equator contact zone) or it would be reduced to a standard bearing (plus the friction at the contact zone) if the head fell into the recess.

German patent DE19915814, entitled "Gelenk-Endoprothese mit verschleissarmer Gleitpaarung," by Manek Buttermilch et al., discloses a ceramic-ceramic total hip prosthesis in which the contact between the two articulating components is a line contact, the line formed by either a modified head geometry or modified cup geometry. In either case, the mismatch is produced by replacing a single radius of curvature by two; the first radius and the second radius have offset centers, resulting in a line contact. Herzian stresses are reduced but not eliminated. The geometry of this invention is also characterized by the fact that the aspherical component of the articulation presents a kink (the two circles defining the cross-section of the aspherical component are not tangent) in its contour at the line of contact.

European patent EP0053794, entitled "Cup for a hip joint," by Manfred Semlitsch, et al., discloses an endoprosthesis in which both the joint ball and the hip joint cup consist of oxide ceramic material. An annular recess is arranged in the area of the opening of the hip joint cup, and a ring of bioinert, plastically deformable material is situated in the recess. The surface of the ring that faces the joint ball merges essentially without interruption and entirely steplessly into the spherical surface of the cup. In the event of subluxation and an associated short-term, linear-type bearing contact between joint ball and joint cup in the edge area of the cup, the result, even in the case of dry friction, is a favourable tribology between the joint ball and the ring of plastically deformable material which comes into engagement with the ball upon subluxation.

European patent EP0821922, entitled "Hip prosthesis joint component with particulate trap," by Claude Hubin and Marie Jean Sterpin, discloses a hip prosthesis cup for metal-metal articulation provided with a polar recess that serves as a trap for wear particles. Alternatively, the head can also have a trap or recess.

French patent FR2727856, entitled "Ensemble prothetique auto-lubrifiant pour Particulation de Ia hanche," by Barba Laurent et al., discloses a hard-hard (metal-metal, or ceramic-ceramic) articulation for a total hip prosthesis. The shape and dimensions are such that a laminar film of synovial fluid can be maintained in use. A reservoir for the fluid is provided at the polar region. No details are provided as to what the geometry of the cup should be to meet the requirement of fluid film lubrication. There is a teaching that the gap between the cup and the head should be in the range of 0.005 to 0.05 mm. This covers the standard radial clearance used in hard-hard bearings.

Great Britain patent GB1322680, entitled "Improvement in and related to prosthesis," by Georges Girard and Ramiro Cameo, discloses a total hip prosthesis in which the surface of the head is provided by a pattern of grooves intended to reduce the wear at the articulation. As prior art, the inventors cite a prosthesis in which the spherical head articulates against a cup that is "football shaped." That is, the cup is elongated, which leads to a line contact, rather than a point contact.

US patent application US2002/0116068, entitled "Containment system for constraining a prosthetic component," by Terry McLean, describes a truncated head within a total hip prosthesis that can be inserted into the cup sideways through slots in the opening of the cup before it is turned into a functional position. As a result, the head is retained within the cup, which covers more than 180 degrees. The unintended result is that the conventional point contact is now changed into a line contact along the edge of the truncated segment of the head.

US patent application US2005/0246026, entitled "Modular orthopedic implant apparatus," by Paul Lewis et al., discloses a modular acetabular cup comprising three elements, that can be combined in different ways to allow the surgeon a choice of implants of varying sizes and features. Fixation is achieved through a central bore through all three components. As in U.S. Pat. No. 6,527,809, one can change the point contact into line contact along the edge of the liner.

US patent application US2005/0261776, entitled "Prosthetic joint with annular contact bearing surface," by Scott Taylor, discloses a truncated, or annular, acetabular component of a total hip prosthesis in which contact between the head and the inner of two members of the cup occurs along a line instead of at a point.

U.S. Pat. No. 5,181,926, entitled "Bone implant having relatively slidable members," by Rudolf Koch and Robert Streicher, describes a total hip prosthesis in which the cup side, within cavities in its polymeric liner, contains self-aligning pads of hard material that articulate against the head.

U.S. Pat. No. 5,549,693, entitled "Cotyloidal prosthesis," by Christiane Roux and Michel Pequignot, discloses a total joint prosthesis in which the cup side contains at its opening a ceramic ring, much like a natural labrum, which forms a seal with the ceramic head. The position of the ring is such that the frictional moment of the couple would be very high.

U.S. Pat. No. 5,593,445, entitled "Bi-axial prosthetic joint," by Thomas Waits, describes a total joint prosthesis in which a third, ring-shaped, member is interposed between the head and the cup. The ring-shaped member increases the contact area under load, between the head and cup self-aligning between the head and the cup in the direction of the load.

U.S. Pat. No. 5,702,456, entitled "Implant having reduced generation of wear particulates," by David Pienkowski, discloses a method of pre-wearing the prosthesis before implantation so the particles usually produced in somewhat higher amounts by the wear-in process do not burden the body. Only a minimal improvement in long term outcome could be expected from such a procedure.

U.S. Pat. No. 5,725,593, entitled "Total anatomic hip prosthesis," by Francesco Caracciolo, discloses a resurfacing total hip prosthesis. The femoral cup has multiple circular rises that are intended to reduce the friction within the spherical cup.

U.S. Pat. No. 5,766,258, entitled "Wrist prosthesis," by Beat Simmen, discloses a wrist prosthesis in which, in one embodiment, one of two separate articulations is produced with non-circular members. The members tend to fall, or self-center, into a stable position in which they become congruent.

U.S. Pat. No. 6,527,809, entitled "Trial acetabulum or implantable acetabulum with adjustable orientation," by Levon Doursounian and Michel Porte, discloses a modular acetabular cup. The cup inlay, which articulates against the head, has a central opening allowing access to a mechanism that locks the cup in a desired position. This, as a side effect, defines the contact conditions between the head and the inlay as a line contact along the edge of the central opening, as is the case in U.S. Pat. No. 4,840,631. "Artificial hip joint socket with hydraulic head support," by Robert Mathys. However, the modular prosthesis described by Doursounian and Porte lacks the hydraulic pressure support disclosed by Mathys.

U.S. Pat. No. 4,031,570, entitled "Prosthetic acetabutum," by Otto Frey, discloses a torus-shaped aspherical cup in which the radius of the curvature is equal to that of the spherical head, but the center of the curvature is offset from the central axis so as to avoid jamming of the head in the cup. This changes the theoretical point contact of a sphere in a spherical socket into a line contact of a sphere in a toroidal socket, and further, for the purpose of improved lubrication, a groove at the periphery of the cup and a recess/pocket at the pole. Herzian stresses are reduced by changing from the point to line contact, but they are not eliminated by the current invention which changes point contact to surface contact.

U.S. Pat. No. 4,840,631, entitled "Artificial hip joint socket with hydraulic head support," by Robert Mathys, discloses a hip joint articulation with a cylindrical recess machined into the cup. This recess creates a reservoir for the joint fluid, which would pressurize under load. Sealing is provided by the edge of the recess. The disadvantage of this arrangement is that high stresses are produced at the edge of the recess, which could lead to localized wear, and potentially to loss of the seal and hence of hydraulic support.

U.S. Pat. No. 5,336,267, U.S. Pat. No. 5,383,936, U.S. Pat. No. 5,738,686 and U.S. Pat. No. 6,312,471, by Dietmar Kubein-Meesenburg et al., disclose the theoretical basis for and solutions to reducing stresses in articulations of joint prosthesis, all of which lead to theoretical line contact instead of point contact. Herzian stresses are reduced, but not eliminated.

GB Patent No. 1322680, entitled "Prosthesis," by Georges Girard et al. discloses a metal-metal total hip joint articulation. The prosthesis includes a concave cup having multiple grooves leaving only protrusions ending on a spherical surface to contact the spherical head. This type of contact is proposed to reduce the risk of jamming of conventional, smooth, spherical surfaces of a ball-in-socket joint, specifically in metal-metal combination, where the required tolerances are tight and difficult to maintain in production.

U.S. Pat. No. 6,645,251, entitled "Surfaces and processes for wear reducing in orthopedic implants," by Abraham Salehi et al. discloses an approach based on grooving the concave surface in order to improve lubrication and distribute the stress. As is known from technical sliding bearings, the main advantage of grooves comes from improved removal of wear particles away from the articulation. Fluid entrapment may play a role in improved lubrication as well. However, grooves as disclosed may in fact lead to higher local stresses at the edges of the grooves and defeat the purpose. There has been no published data supporting the concept and no evidence of acceptance of this approach by the orthopedic device industry.

U.S. Pat. No. 6,425,921, entitled "Sliding partners for artificial joint implants," by Hans Grundei and Wolfram Thomas, discloses an alternative approach where grooves are produced in the convex component of the joint. Actual hip simulator tests performed on this type of joint components did not show any wear reduction.

Practical limitations on the accuracy of the machinable components, including the effects of temperature and of radiation-induced shrinkage (which may be used for sterilizing polymeric cups) and the need for safety precautions (e.g., against jamming of the components when used in the body) have led to international standards which help to guarantee acceptable in viva performance.

ISO standards 7206-2; 27.80 to 28.00 and 7206-2; 28.10 to 28.30 specify the geometry and dimensions of the head and cup components, respectively, of a total hip prosthesis. For example, regarding the sphericity and dimensional tolerance of the head component, the standard specify that the metal or ceramic femoral head component of a total hip prosthesis shall have a departure from roundness of not greater than 10 micrometers. If used against hard material cups (metallic or ceramic) it will not be greater than 5 micrometers. The diameter shall be equal to nominal diameter +0.0, −0.2 mm. For metal-metal or ceramic-ceramic articulations the tolerances are not specified, but in all cases there shall be radial clearance. In practice, the heads in use today are produced with significantly tighter specifications than required by the standards.

Regarding sphericity and dimensional tolerance of the cup component, for polymeric components, the sphericity is not specified. For hard materials, it shall not exceed 5 micrometers. The dimensional tolerance for a polymeric cup is +0.3, +0.1 mm at 20±2° C. from the nominal diameter. In practice, UHMWPE cups are oversized by at least +0.2 mm over the nominal diameter. No tolerances for the metallic or ceramic cups are given, but the radial clearance must be guaranteed by the producer. Typical radial clearance for hard pairs is in the range of 0.02 to 0.03 mm.

SUMMARY OF THE INVENTION

The present invention features artificial joint articulations and articulating total joint prostheses including an artificial joint articulation as described herein. In various aspects, the present invention features artificial joint articulations and articulating total joint prostheses including a convex member (which we may also refer to as a "head") and a concave member (which we may also refer to as a "cup" or "fossa"). It is to be understood that where features are described with respect to an artificial joint articulation, those features can also be present in a total joint prosthesis that includes such an artificial joint articulation.

In one aspect, the artificial joint articulation includes (1) a convex member comprising a surface curvature on at least a portion thereof and (2) a concave member comprising a surface curvature on at least a portion thereof. The surface curvature on the convex member is different from the surface curvature of the concave member. Where the convex and concave members interact, they define ring-like areas of contact on their surfaces, and those areas are further defined by the inclusion of a material that is distinct from, or has distinct characteristics from, the material peripheral to the areas of contact. Generally, the material defining a ring-like area of contact is harder that the materials peripheral thereto. For example, the cup can be formed of ultra-high molecular weight polyethylene (UHMWPE) or a comparable polymer and can include an insert of a harder material (i.e., harder relative to the material forming the remainder of the cup) such as a metal, a ceramic, or a cross-linked UHMWPE. To distinguish the materials, we may refer to the material within one articulating member that does not come into contact with another articulating member as the "first" material, and we may refer to the material within one articulating member that does come into contact with another articulating member as the "second" material. Unless the context indicates otherwise, the second material will be harder than the first.

The second material can form an integral or integrated part of the device (e.g., an artificial joint articulation or an articulating total joint prosthesis), appearing to be substantially seamless with respect to the first material. Alternatively, the second material can be non-integral. For example, the second material can be defined as an insert that is shaped and positioned within either member (i.e., within the concave head or the convex cup) so as to form a contact surface with the other member. The insert can be formed so as to be held within the cup (e.g., a cup fashioned from or including UHMWPE). Thus, where the second material is non-integral, the member in which it resides may also include a recess into which the second material or "insert" is inserted.

As noted, the geometry of the head and cup can conspire to form a desired contact surface. The contact surface includes a circular area of substantially spherical shape about an axis of revolution, and it is for that reason that we refer to it as "ring-like." The second material, whether integrated or present as a defined insert, can be positioned at a contact surface as determined by the geometry of the head and cup. In one embodiment, a spherical head (within either an artificial joint articulation or an articulating total joint prosthesis (e.g., a total hip prosthesis)) articulates with an aspherical cup, with a theoretical surface contact over a band centered at about 45 degrees from the axis of rotation. In one embodiment, a portion of the head is spherical, and that portion can be the portion that resides within the cup. The insert may be positioned symmetrically or asymmetrically within the cup. For example, the insert in any embodiment may be positioned asymmetrically so as to be centered around an axis of major in vivo loading.

Generally, the area of the concave member or cup fashioned from the first material provides the desired elasticity and shock absorption for the joint, while the second material (e.g. in an insert within the cup) provides reduced wear. The surface of the convex member (e.g., a spherical head) can be highly polished. The second material at the contact surface (e.g., an integrated region or insert) can retain a degree of roughness that is generated, for example, with multiple indentations. For example, one can use a machining process to create a plurality of high points (e.g., circular high points) on the contact surface of the insert such that corresponding indentations are formed on the surface. In various embodiments, the high points can be rounded or flattened.

In one aspect, the invention features joint articulation or an articulating total joint prosthesis that includes (a) a convex member having a first surface curvature on at least a portion thereof and (b) a concave member having a first surface curvature on at least a portion thereof. The surface curvature on the convex member is different from the surface curvature of the concave member; the convex member and the concave member each have an articulating surface and interact with one another at a contact surface; and the material present at the contact surface is harder than the material peripheral to the contact surface. For example, the convex member or head can be spherical and the concave member or cup can be aspherical. As noted, we may refer to the harder material as a "second" material to distinguish it from the surrounding or peripheral material. The harder material may be present at the articulating surface of the convex member, the concave member, or both. In the illustrations provided, the second material is provided at the articulating surface of the convex member as an insert within an accommodating recess.

In one embodiment, the invention features an artificial joint articulation or an articulating total joint prosthesis comprising: (a) a convex member having a first surface curvature on at least a portion thereof; (b) a concave member comprising (i) a first material having a second surface curvature different from that of the first surface curvature and (ii) an annular recess comprising an annular insert of a second material. As noted, in this embodiment and the others described herein, the second material is harder than the first material and can have an inner surface congruent to the first surface curvature of the convex member. Thus, the annular insert can be positioned within a recess of the concave member.

As noted, the first material can be Ultra High Molecular Weight Polyethylene (UHMWPE) and the second material can be any material that is harder than UHMWPE (e.g., a metal, a ceramic, or a cross-linked UHMWPE). The convex member can be fashioned of metal or ceramic.

The first surface curvature can be spherical and the articulating surface (e.g. an insert) can be positioned about a loading point of the joint.

The joint prosthesis overall can be configured according to methods known in the art for use as a replacement hip joint, knee joint, spinal disc joint, finger or toe joint, elbow joint, or a wrist or ankle joint.

The inner surface of an articulating or contact surface (e.g., an insert) can include a plurality of imperfections thereon and a plurality of indentations between the imperfections. For example, each of the plurality of imperfections can include a plurality of knobs thereon.

The surface of the convex member can be hard-coated by titanium nitride, chromium nitride, aluminum oxide or a diamond-like coating. The inner surface of the insert can also be hard-coated by titanium nitride, chromium nitride, aluminum oxide or a diamond-like coating.

While we refer to "an artificial joint articulation," it is to be understood that the invention encompasses the articulating members of an artificial (i.e., non-naturally occurring) device per se as well as a prosthesis that incorporates such members together with other component parts. For example, the invention features articulating members (e.g., a head member and a cup member as described herein) that may be manufactured, packaged, or sold separately from other members of the prosthesis (e.g., separately from a stem for immobilizing the head member in the shaft of a bone). When made, packaged, or sold separately, a surgeon may then select and assemble the articulating members described herein with other component parts to best accommodate a particular joint and provide a more customized prosthesis for a given patient. The articulating members can be incorporated in any prosthesis that generates line contact (e.g., a ring-shaped line of contact) between a convex head member (or "ball") and a concave cup member (or "socket").

The insert described herein may also be manufactured, packaged, or sold separately and is also an aspect of the present invention in and of itself.

While the various devices described herein are clearly intended to be configured for human use, the invention encompasses veterinary use as well. Accordingly, in another aspect, the invention features methods of repairing or replacing a damaged or defective joint in a patient. The methods can include a step of identifying a patient in need of treatment and administering (for example, by surgical implantation) a device as described herein.

BRIEF DESCRIPTION OF THE DRAWINGS

FIG. 3a is a perspective view of an insert according to an embodiment of the invention.

FIG. 3b is a cross sectional view of the insert of FIG. 3a.

FIG. 3c is a cross sectional view of another insert according to an embodiment of the invention.

DETAILED DESCRIPTION

For the sake of simplicity and clarity, we illustrate the artificial joint articulation and the prostheses of the invention with a total hip joint articulation. The same technical principles and design can be used for articulations of other joint prostheses, including those having less conforming surfaces and a lesser degree of coverage. The present invention represents an improvement over a prior invention by the inventors as set forth in PCT Patent Application No. WO2008/058756, published on May 22, 2008, and over that of U.S. Patent Application Publication No. 2010/0063589 entitled "Wear-reducing Geometry of Articulations Total Joint Replacements" which is incorporated herein, in its entirety, by reference (collectively, "the Tepic Applications"). The Tepic Applications disclose a joint prosthesis, such as a hip prosthesis, in which the convex and concave components differ in shape to provide a broad contact surface. As set forth in the Tepic Applications, the differences in shape between the components further provide improved lubrication of the components and particularly the contact surface. While that structure results in significantly reduced wear, wear may still be somewhat of a concern, particularly when the concave component is formed of UHMWPE. The wear can be further reduced by the present invention in which one or both members of an articulating pair (e.g., a concave component of UHMWPE) includes a region (e.g., an insert) of cross-linked UHMWPE or another material with increased hardness at the contact surface. Prosthetic devices with the improved members described herein are expected to wear better as they include a material at the contact surface (e.g., the annular or ring-like portion of the convex head and concave cup that engage upon loading) that is harder than the material used elsewhere in the non-articulating regions of the members.

Figure 1:
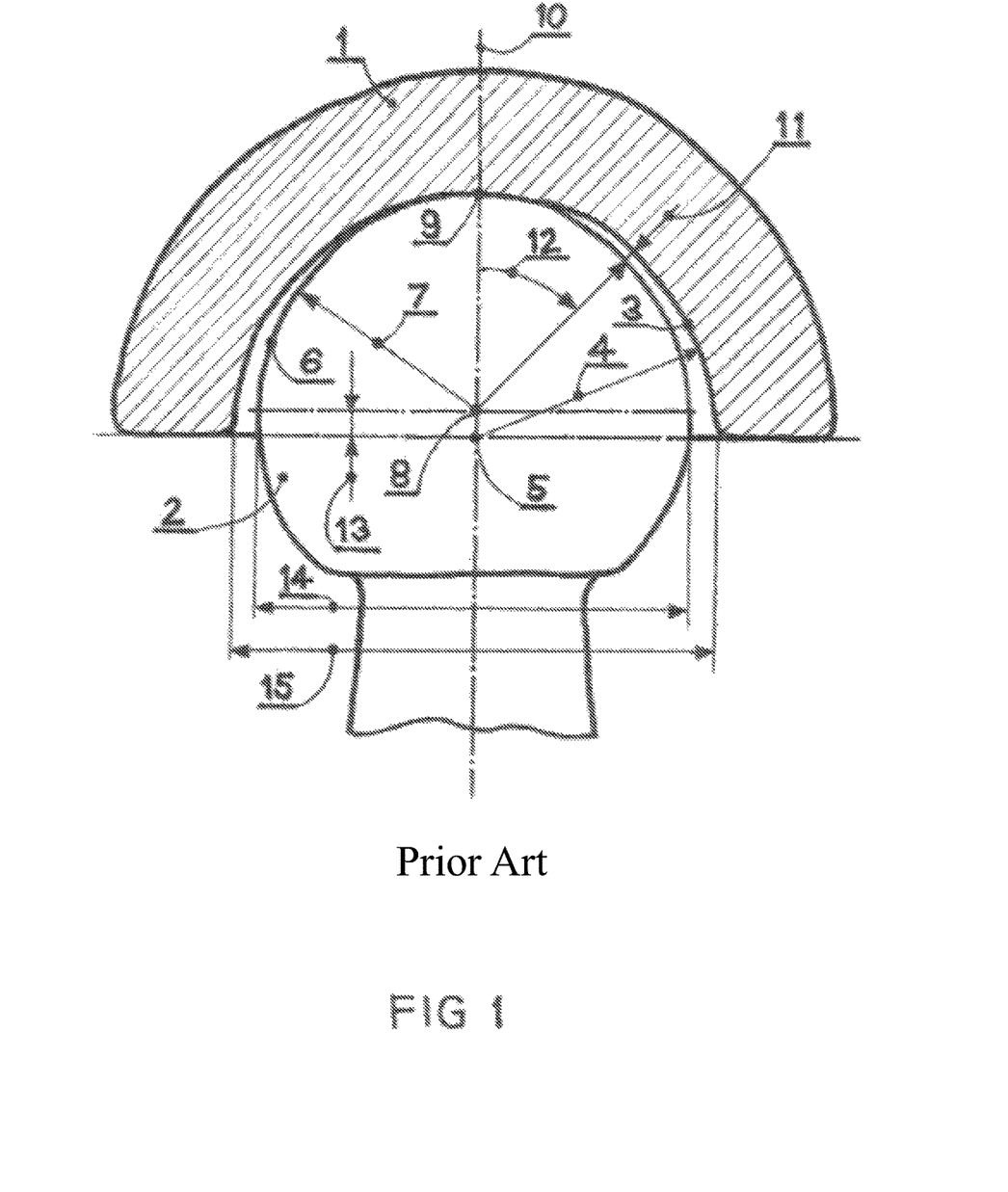
FIG. 1 is a schematic cross sectional view of an artificial hip joint articulation according to current standards.

FIG. 1 illustrates a conventional, standardized total hip prosthesis articulation, with a spherical convex component, or head, 2 seated into a spherical concave component, or cup, 1. The theoretical contact between them is at a point 9, provided that the load is oriented along axis 10. The articulating surface 3 of the cup 1 is of spherical shape with a radius 4 centered at point 5. The surface 6 of the head 2 is also spherical of radius 7 centered at point 8. The shapes of the two components are axisymmetric, i.e. both are bodies of revolution and can be described in a polar coordinate system, with the origin 8, the polar axis 10 and the polar angle 12. The gap width 11 is zero at the polar angle 12 of zero degrees, i.e. at the pole; it approaches maximum radial clearance equal to the difference between the radii 4 and 7 at the polar angle of 90 degrees. Distance 13 between the points 5 and 8 is equal to the difference between the radii 4 and 7, i.e. 13 is the radial clearance. For UHMWPE cup liners and metal or ceramic heads the usual radial clearance is in excess of 0.1 mm; for metal-metal pairing it is usually less than 0.03 mm.

Diameter 15 of the cup opening is larger than the diameter 14 of the head 2, so that the head 2 can freely come into its seat within the cup and make the contact at point 9. Under load the point contact will spread out into a surface contact, resulting stresses being known as Herzian, after Heinrich Hertz, who with his 1882 classic publication has provided the theoretical basis for calculating contact stresses between bodies of simple geometrical forms (Hertz, H.: "Gesammelte Werke," Vol. 1, Leipzig, 1895). Formulas to calculate Herzian stresses are given in e.g. "Formulas for Stress and Strain," Fifth Edition, Roark and Young, McGraw-Hill, 1982, Chapter 13. The subject is extensively covered in e.g. "Contact mechanics," K. L. Johnson, Cambridge University press, 1985. For a sphere in a spherical socket the formulas are valid only if the radius of the socket is larger than that of the sphere; improved formulas for closely matching radii have also been developed, but if the radii are equal, the contact stress in the Herzian sense is eliminated.

Figure 2:
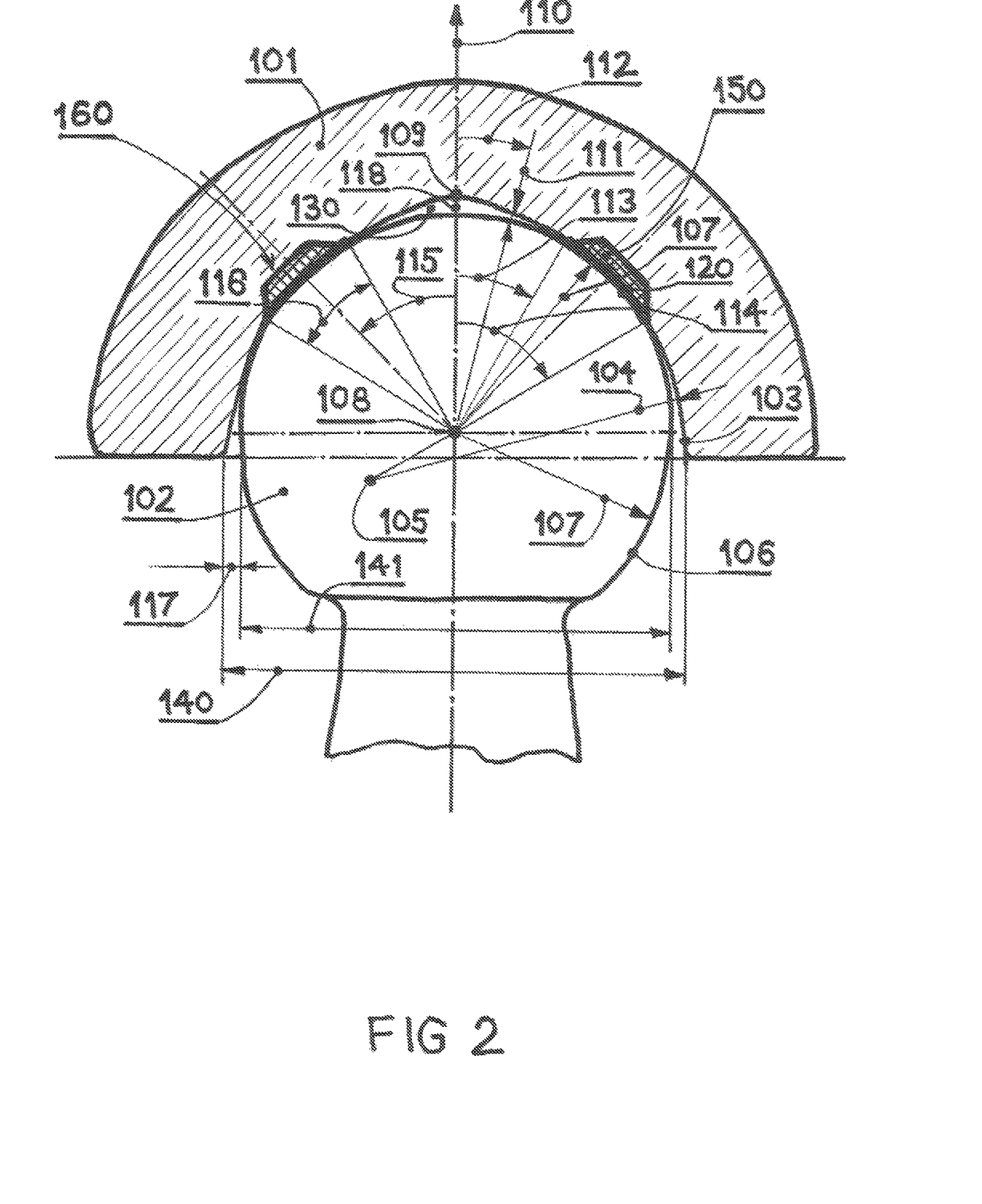
FIG. 2 is a schematic cross sectional view of an artificial total hip joint articulation according to the invention, showing a spherical head in an aspherical, fossa cup.

FIG. 2 shows the head 102 in the cup 101 articulation according to shapes set forth in the Tepic Applications and according to the present invention. As more fully set forth in the Tepic Applications, the head 102 is spherical with its surface 106 having a radius of curvature 107 with the center at the point 108. The articulating surface 103 of the cup 101 is aspherical—more precisely—only partially spherical, axisymmetric around the axis 110. Over an arc 120, between the polar angles 113 and 114, the surface 103 is spherical, congruent to the head surface 106. In 3D the arc 120 defines a band 121 of theoretical contact, a section of a spherical surface, FIG. 2a.

For polar angles larger than 114 the radius of curvature 104, of the surface 103, with the center at 105, is larger than the radius 107, opening a gap between the two articulating surfaces 103 and 106.

For polar angles just smaller than 113, the radius of curvature of the surface 103 is also larger than of the surface 106, again opening a gap 111. As the polar angle approaches zero, the radius of curvature of the surface 106, is decreased to round off the shape of the cup at the pole 109. The resulting gap at the pole is 118.

The arc of circle 120 of perfect congruency is centered at the polar angle 115, and its corresponding width angle is 116.

The position, 115, and the width, 116, of the band of theoretical surface contact are subject to parametric optimization. First order approximation suggests that the angle 115 should be about 45 degrees; the width 116 about 30 degrees. Theoretical optimizations, coupled with experimental testing, including a cost-function placed on the frictional moments of the articulation, are expected to place the angle 115 into the range between 20 and 50 degrees; the surface contact width 116 into the range between 10 and 40 degrees.

Figure 2A:
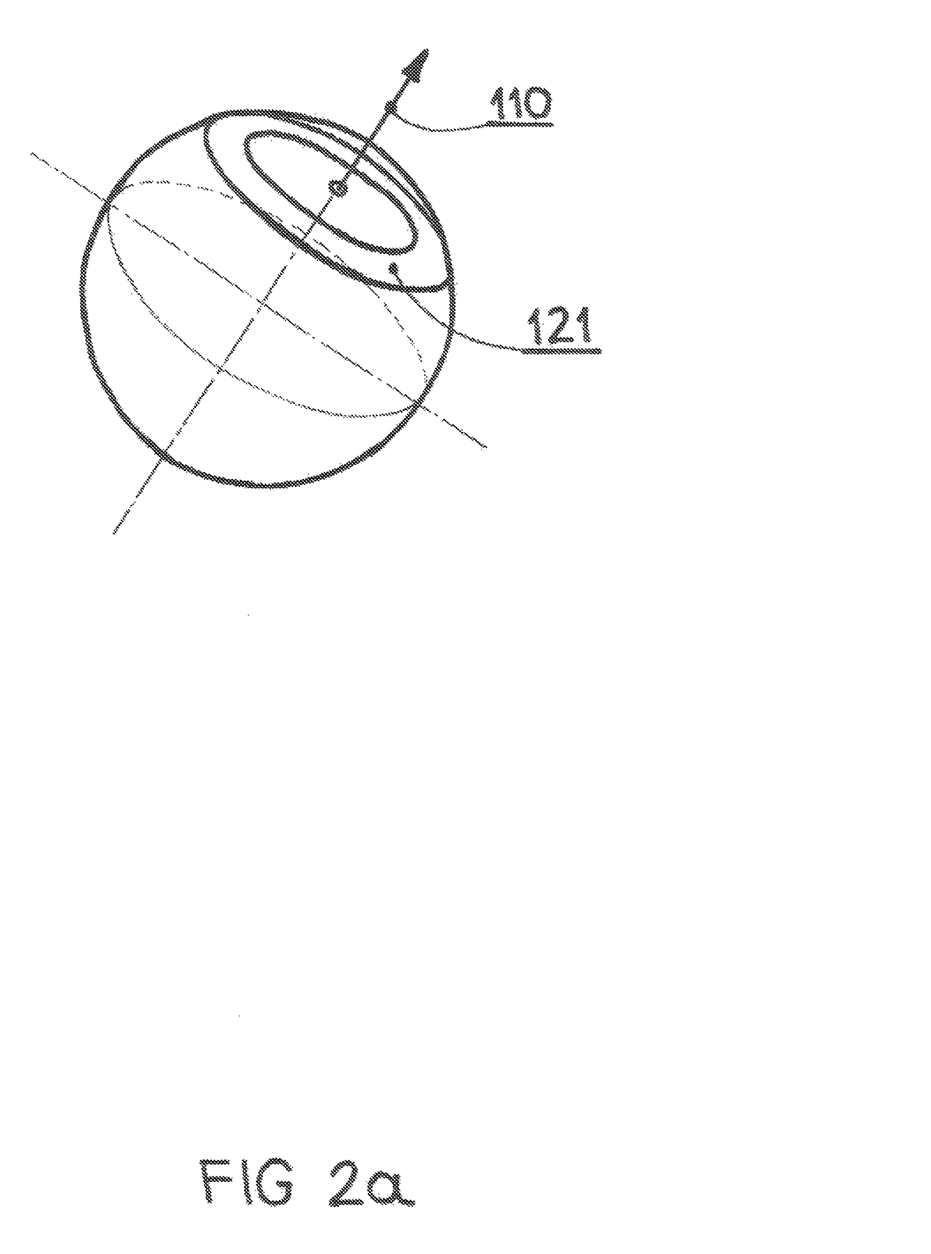
FIGS. 2a and 2b illustrate the contact surface for the artificial total hip joint articulation of FIG. 2.

The contact surface or band of contact 121, shown in a perspective view on FIG. 2a, is defined by the arc 120. The aspherical shape of the cup forms a volume 130, at the polar aspect between the surfaces 106 and 103 of the head and the cup, respectively, within the band of contact 121.

Opening 140 of the cup is larger than the diameter of the head 141, resulting in the clearance 117, so that the head is free to seat itself into the cup generating a surface contact along the area 121.

The type of cups shown in FIG. 2 will be referred to as fossa type. Fossa in general means a cavity, or depression, and in case of the hip acetabulum, it is a centrally located recessed area not covered by cartilage.

The scale of the fossa gap is greatly exaggerated on this and on the following figures. In reality, it will depend on the materials used. For an UHMWPE cup of the fossa type the maximum gap size, which conveniently would be 118 at the pole 109, should be big enough, so as to avoid bottoming out of the head 102 even after maximum anticipated use of the prosthesis, e.g. for 50 years. Wear tests have suggested the rate of about 4 micrometers per million cycles of loading, which may correspond to 1 to 2 years of in vivo use. To allow for 50 years of wear without bottoming out, the gap 118 should be 0.2 to 1 mm; 2 mm would give a safe margin, but this may call for fairly significant changes of the radius vector 104 for the polar angles between the axis 110 and the first angle of contact 113.

Figure 2B:
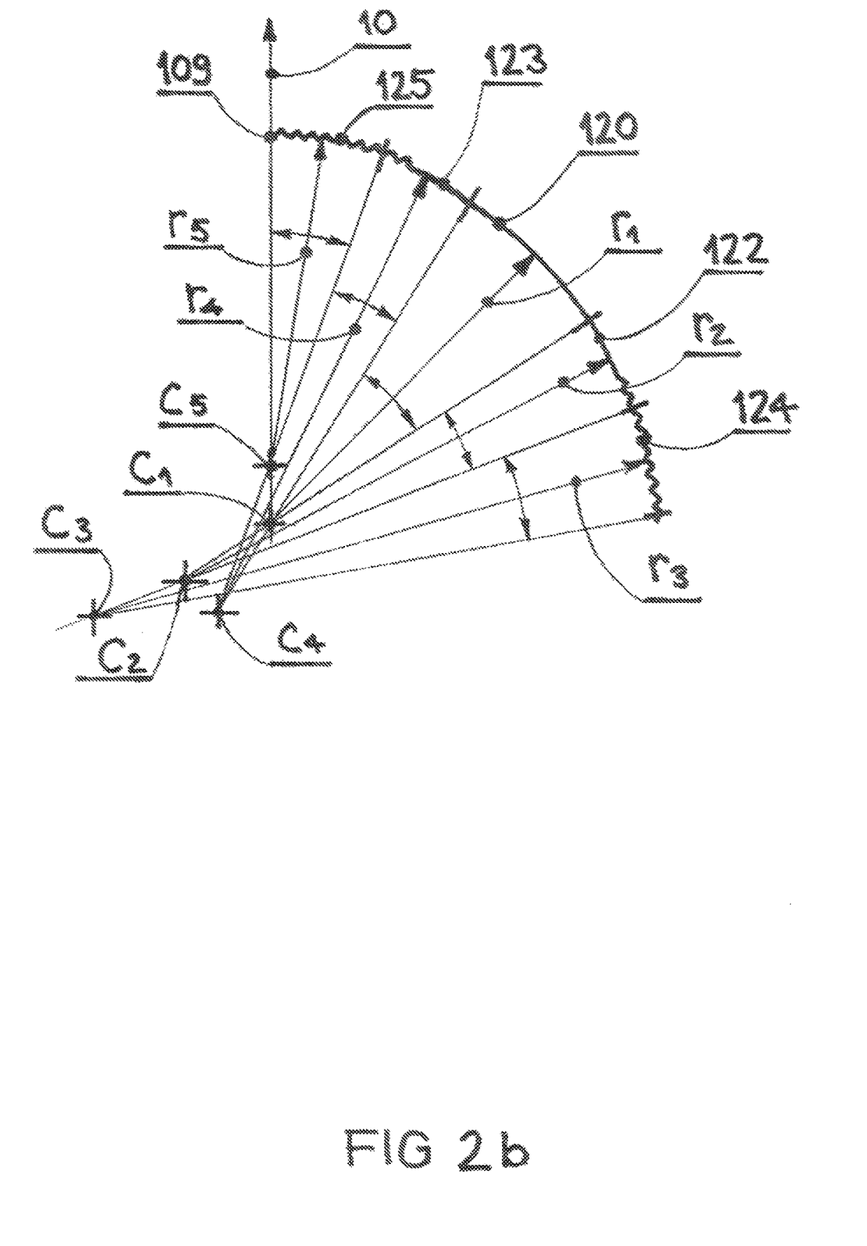

Ideally, the changes of the radius of curvature of the surface 103 below and above the angles 113 and 114, respectively, should be continuous, but for practical reasons one or two steps will suffice, especially if machined in the soft polymeric materials like UHMWPE. It is highly preferable, though, that the transitions are tangential, i.e. that the contour of 103 is smooth, as shown in FIG. 2b. Radius r1 of the arc 120 centered at C1 is the nominal radius, equal to that of the head. Radius r2, corresponding to the arc 122, is centered at C2 and is larger than r1. As shown, the centers C1 and C2 should be placed on the radi-vector defining the transition from 120 to 122, so as to make the transition smooth, i.e. there is a common tangent to the arcs 120 and 122 at the transition point. Radius r3 with the center C3 defines the arc 124; r4 with the center at C4 the arc 123; radius r5, with the center at C5 the arc 125.

A ring shaped insert 150 is embedded in the cup 101, FIG. 2. The insert 150 is illustrated in FIGS. 3a and 3b. The insert 150 has a concave inner surface 151. The inner surface 151 corresponds to the shape of the cup 101 at the band of contact 121. Preferably, the width of the insert 150 generally corresponds to the width of the band of contact 121 or is slightly wider so that substantially all contact between the head 102 and cup 101 occurs at the inner surface 151 of the insert 150. The cup 101 can be formed of UHMWPE. The cup includes a recess 160 positioned and shaped to receive the insert, FIG. 2. The insert 150, on the other hand, is of a harder material, such as metal or ceramic. Alternatively, the insert 150 may be of cross-linked UHMWPE. In this manner, the cup 101 provides the desired elasticity and shock absorption, while the insert 150 provides reduced wear.

Figure 3:
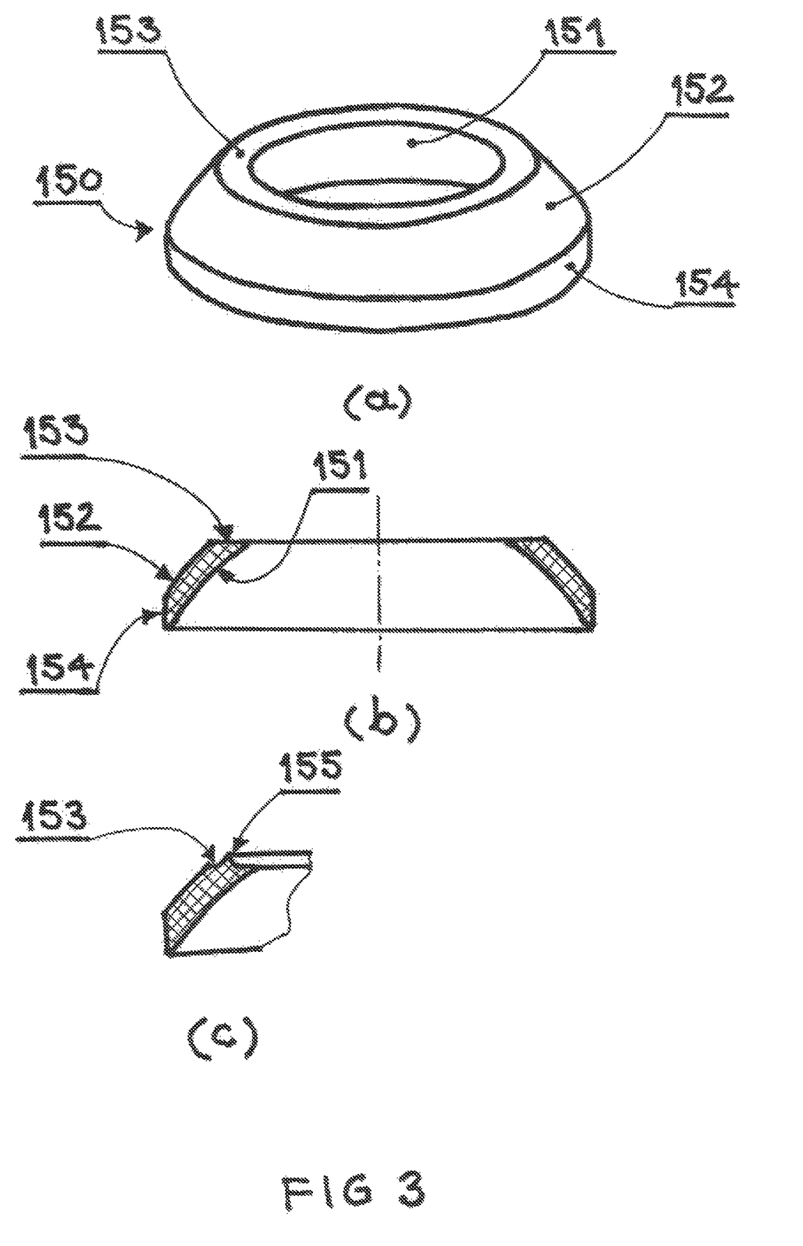

As shown on FIG. 3, the insert 150 has an outer surface 152, upper surface 153, and lower surface 154, which abut the UHMWPE portions of the cup 101 within the recess 160. The outer surface 152, upper surface 153, and lower surface 154 may have various shapes. Preferably, the depth of the insert 150, between the inner surface 151 and outer surface 152 is small so that the insert is flexible. The outer surface 152 may be parallel to the inner surface 151, or may have a different shape. The upper surface 153 and lower surface 154 are shaped for ease of insertion and to provide retention of the insert 150 within the cup 101. According to one embodiment, shown in FIG. 3b, the upper surface 153 and lower surface 154 are transverse to the outer surface 152 such that the outer surface 152 is smaller than the inner surface 151. The recess 160 is dimensioned so that fully inserted ring 150 undergoes a snap fit with a residual press fit. In the previously described embodiments, the upper surface 153 and the lower surface 154 are planar. The upper surface 153 and lower surface 154 may have various other non-planar shapes and may include discontinuities to provide desired interaction with the cup 101 and to help retain the insert 150 in place. For example, as illustrated in FIG. 3c, the upper surface 153 may be provided with a sharp ridge 155, which at insertion creates an indentation in the cup 101, thus improving the sealing of the back side of the ring 150 and the recess 160.

To minimize the production of wear, international standards (ISO, ASTM) have proposed the upper limits on the roughness of the articulating surfaces: (i) UHMWPE cup maximum Ra of 2 micrometers (approximately grade N7); today, UHMWPE cups are typically machined to surface roughness of N5 to N6 corresponding to Ra of 0.4 to 0.8 micrometers; (ii) metal or ceramic heads maximum Ra of 0.05 micrometers (grade N2); ceramic heads are typically finished with Ra of less than 0.01 micrometers.

Notwithstanding the value of the standards, in light of the importance of maximizing the efficiency of dynamic lubrication, the surface finish of the inner surface of the cup, and particularly of the UHMWPE cup, should not be uniform over the entire surface. The unloaded, theoretical surface contact over the arc 120, FIG. 2b, under load will spread out to a wider band towards the pole 109 by a partial width of the arc 123 and towards the equator by a partial width of the arc 122. This broader band of contact represents the envelope for major loading vectors across the joint, not only a static, single position/load. All of this surface can be machined to a high degree of smoothness, e.g. N5. The rest of the cup surface, in order to maximize dynamic resistance to fluid flow out from the pressurized pool 130, can have a higher degree of roughness, preferably at about grade N12, corresponding to Ra of 50 micrometers. As suggested on FIG. 2b, a preferred texture can be one in which grooves run at 90 degrees to the direction of flow, which naturally would be the result of machining the cup by turning its inner surface, as is most commonly done. The desired roughness can be achieved by machining the insert 150 to a higher degree of smoothness than the cup 101. The cup can be provided with a uniform degree of smoothness.

With the use of the insert of the present invention, the formation of metal-metal and ceramic-ceramic combinations is simplified. Spherical surfaces can be formed on all of the metal or ceramic parts, i.e. the head and insert. The non-spherical surfaces can be formed within the cup without regard to the spherical surface. Once formed, the insert is positioned within the cup and provides the desired spherical surface to interact with the head.

To maximize benefit, the axis 110 can be directed into the window of functional, physiological force vectors acting on the articulation. Thus, the insert can be preferably centered about the location of the principal force vector. The prior embodiments have illustrated the insert 150 as being centered within the cup 101 because the force vector was presumed to be through the center of the cup. For various joints, the force vector may not pass through the center of the cup. The insert can be offset to provide the contact surface at a corresponding proper location for such joints.

Figure 4:
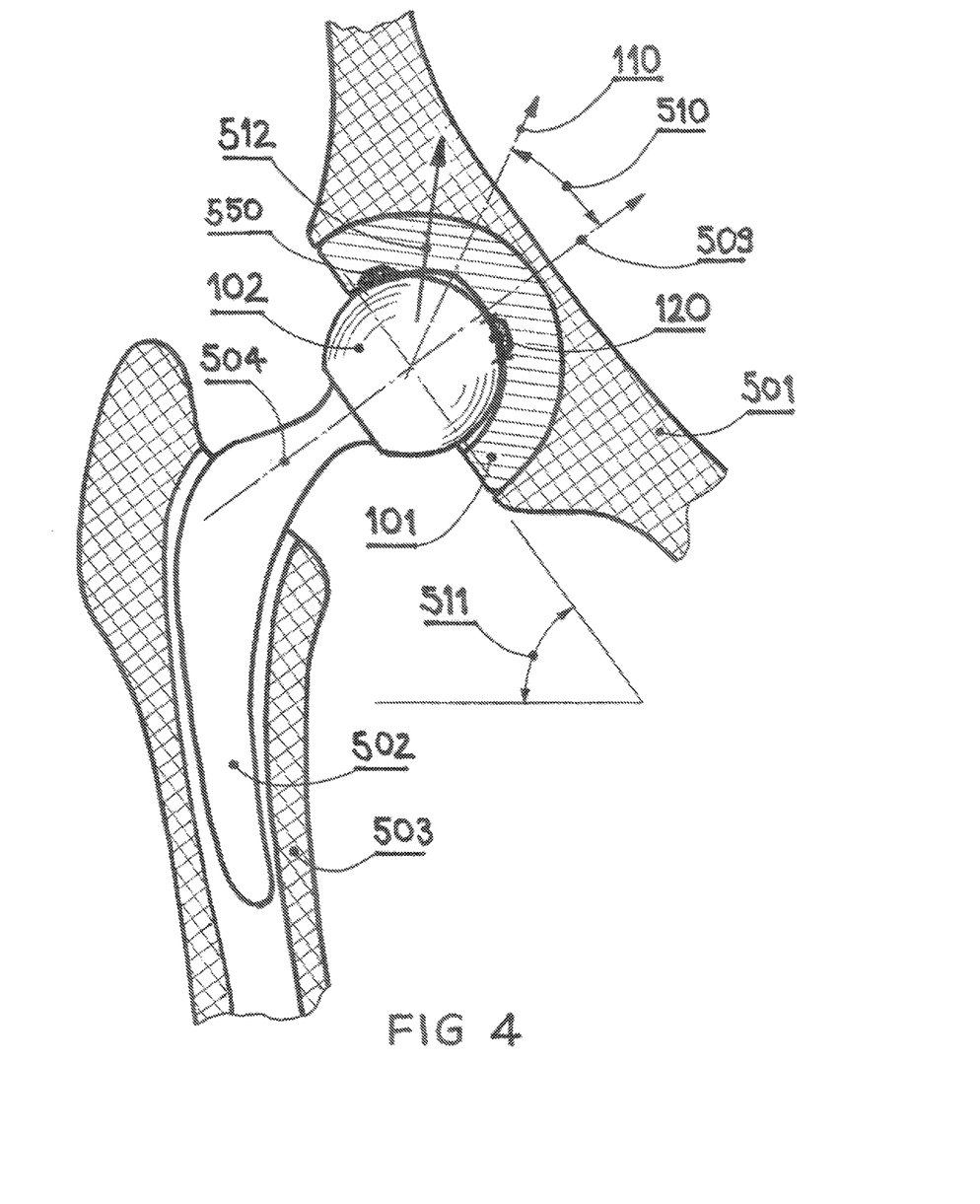
FIG. 4 is a cross sectional view of the artificial total hip joint according to the invention, showing a spherical head in an aspherical, fossa cup. The axis of symmetry of the cup inner shape and the position of the insert are offset from the main axis of the cup, so as to place the fossa of the cup into the window of major joint force vectors acting on the cup in actual use.

FIG. 4 is a schematic representation of a total hip prosthesis, with the cup 101 inserted into pelvic bone 501 and the head 102 affixed to the femoral stem 502 which in turn is inserted into the femur 503. The axis of the femoral neck is 504. The axis 110 of the fossa geometry of the cup 101 and of the insert 550 is offset from the main axis 509 of the cup, by an angle 510. If the angle 510 is approximately 25 degrees, and the cup is inserted at an angle of lateral opening 511 of approximately 45 degrees the arc of contact 120 (corresponding to the band of contact 121, FIG. 2*a*) centered on the axis 110, will meet the requirement to encompass most of the physiological load vectors 512 transmitted from the head to the cup. The cup should also be inserted with an angle of so-called anteversion (pointing forward) of about 10 to 15 degrees (e.g., about 10, 11, 12, 13, 14, or 15 degrees). Such a cup must be clearly labeled for the surgeon to be able to orient it properly at insertion. In keeping with this embodiment, any of the present devices can be configured such that the axis of symmetry of the cup inner shape and the position of the insert are offset from the main axis of the cup. This places the fossa of the cup into the window of major joint force vectors acting on the cup when it is in actual use.

Figure 5:
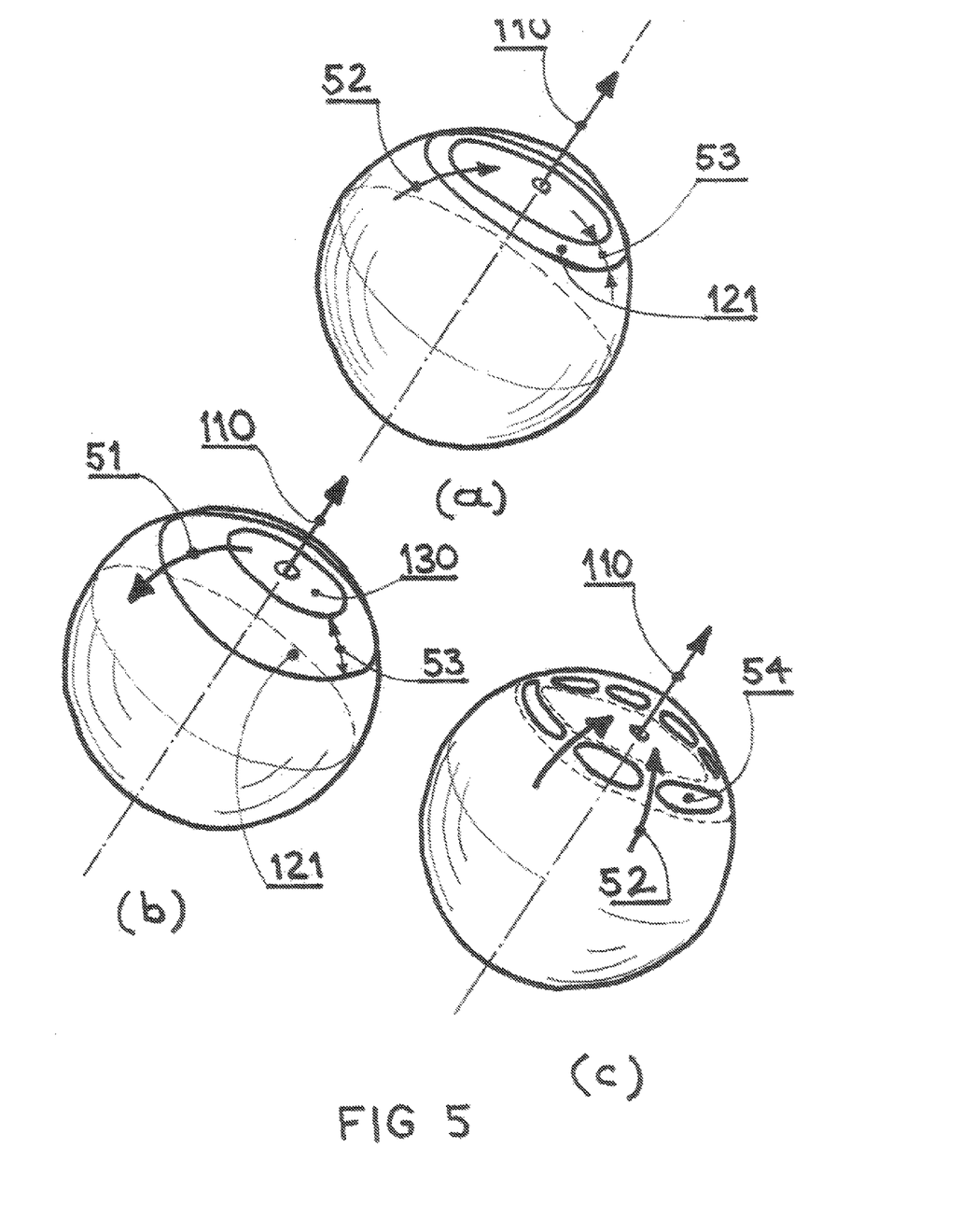
FIGS. 5a-5c are perspective views of a total hip articulation showing contact areas under differing load conditions.

FIG. 5 shows a perspective view of the contact area 121 of the articulation of a fossa-type cup under loading. Due to the elasticity of the components, the area of contact can vary and can spread out from the original annular surface contact, as shown in FIG. 5*a*, to a wider area of surface contact as shown in FIG. 5*b*. The insert 150 may be formed to provide the total contact width 53 (FIG. 5*b*), or the original contact width 53. The width 53 of the contact area 121 is load dependent. When the load is high (or as the load increases), the fluid from the pool 130 is pushed out, as shown by arrow 51, through the interarticular gap over the area 121, across, now, the longer distance 53, FIG. 5*b*. As the load is reduced, the elastic recoil of the components will tend to increase the volume of the pool 130 and thus draw the fluid back in, as shown by the arrow 52, FIG. 5*a*. In this phase, the contact area is narrowed, i.e. 53 is reduced, and thus there is less resistance for the re-filling of the pool 130. This can be important, since the maximum underpressure which can pull the fluid back in is 1 bar, while much higher pressures can be induced during the draining, high load, phase. The use of the insert further enhances the flow of fluid to and from the pool 130. By accident or design there will be gaps along the circumference of the contact area with contact areas 54, FIG. 5*c*, leaving channels for fluid to flow 52 into the volume 130 when the load is reduced. The depth, or the thickness, of the insert 150 can be made so small that the contact pressure on the contact areas 54 under load will flatten out the insert waviness and seal the gaps.

Figure 6:
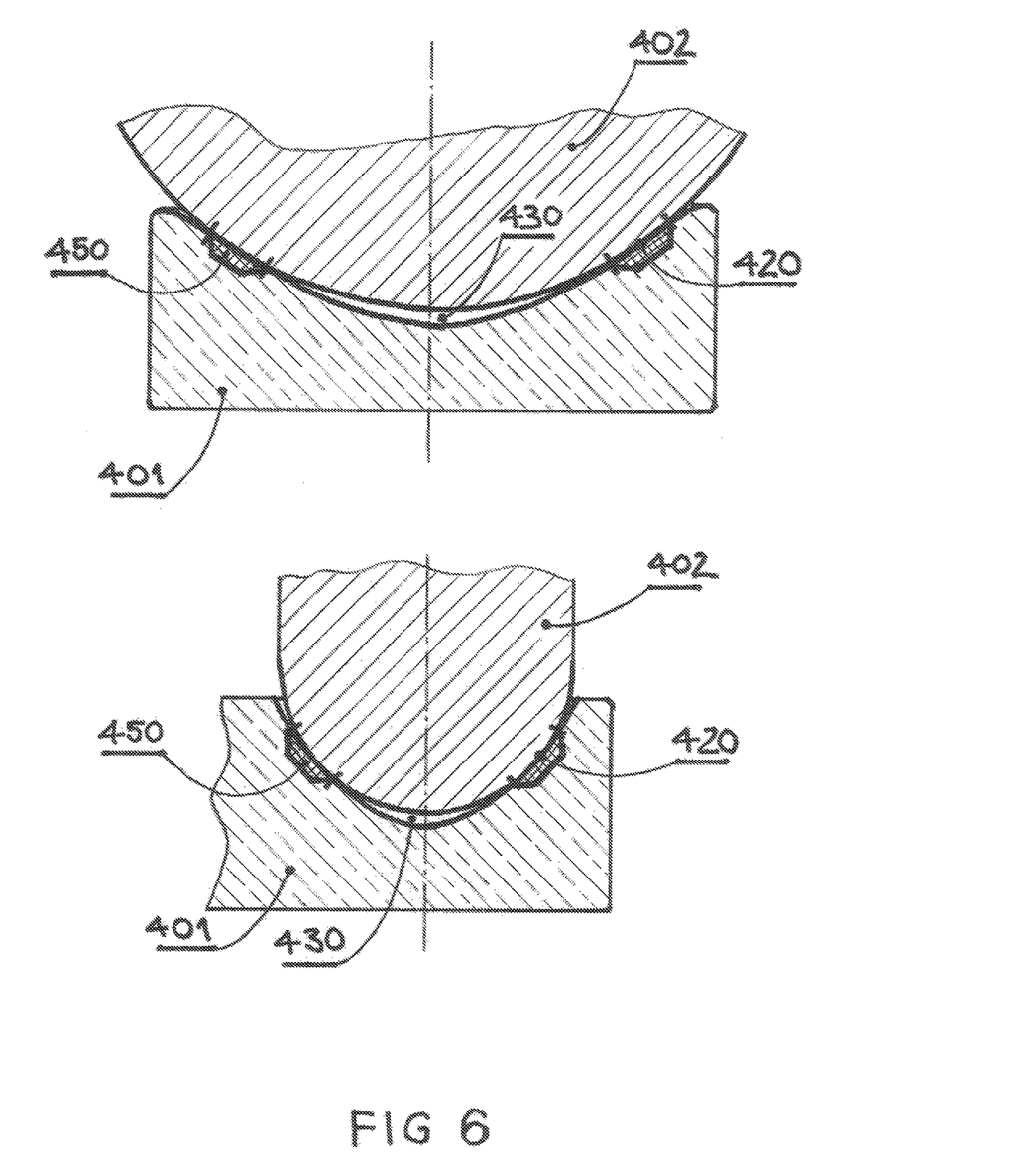
FIG. 6 is a pair of perspective views of the tibial plateau of a partial or a total knee prosthesis showing a fossa feature.

FIG. 6 shows saggital and frontal sectional views of a knee condyle prosthesis with the femoral component 402 making a surface contact 420 against the tibial plateau 401, produced from UHMWPE, of the fossa type. The area of the tibial plateau 401, which normally would be exposed to highest stresses, is now slightly recessed defining the pool 430, providing for the above-explained means of load distribution and dynamic lubrication. The femoral component being shaped as a torus, the two sectional views differ only in the respective curvatures of the articulating components. The insert 450 is positioned within the UHMWPE of the tibial plateau 401. While in the prior embodiments, the inserts were circular in shape, the insert 450 for this embodiment would be non-circular. The shape depends upon the geometry of the components to provide the desired contact surface 420.

Figure 7:
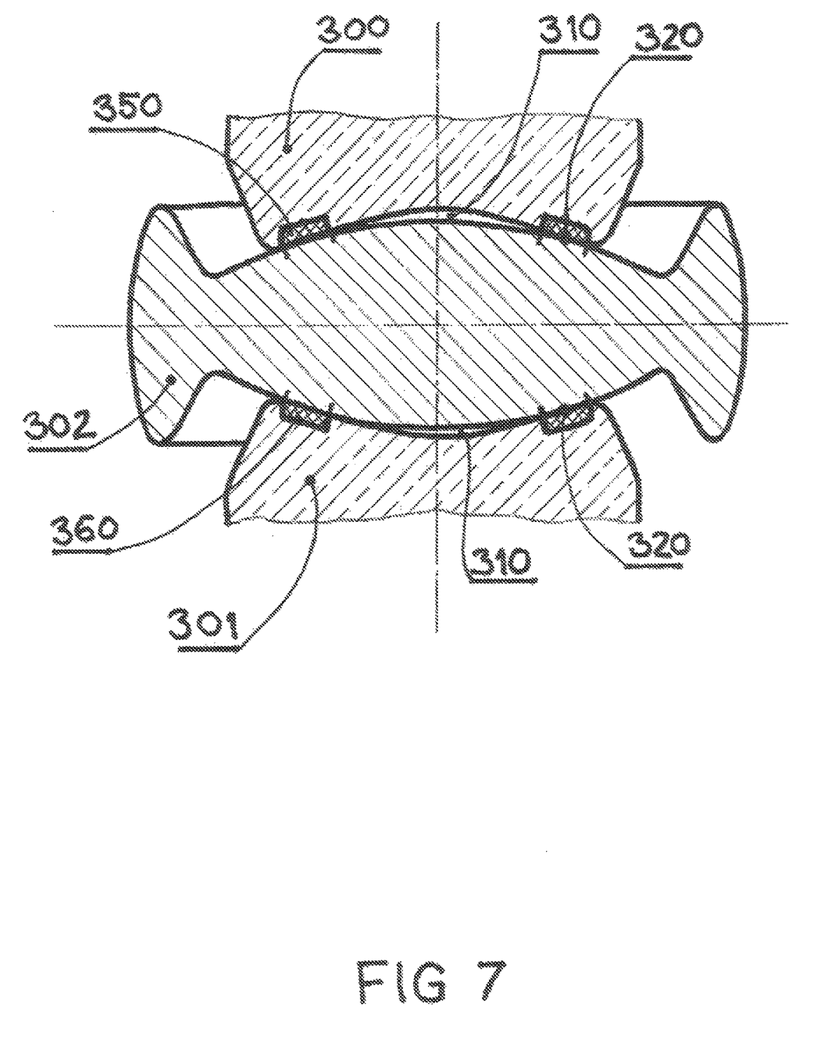
FIG. 7 is a cross sectional view of a spinal disk prosthesis according to the invention.

FIG. 7 shows a spinal disc prosthesis according to the invention. The central, lens-shaped body 302, made from a hard material such as ceramic, or metal, articulates on both of its faces against concave components 300, 301, produced preferably from a softer material such as UHMWPE, along surfaces 320, so as to leave gap volumes 310 filled with fluid, providing again for the above-explained means of load distribution and dynamic lubrication. Inserts 350, 360 are positioned within the concave components 300, 301 to provide the desired contact surfaces 320.

Figure 8:
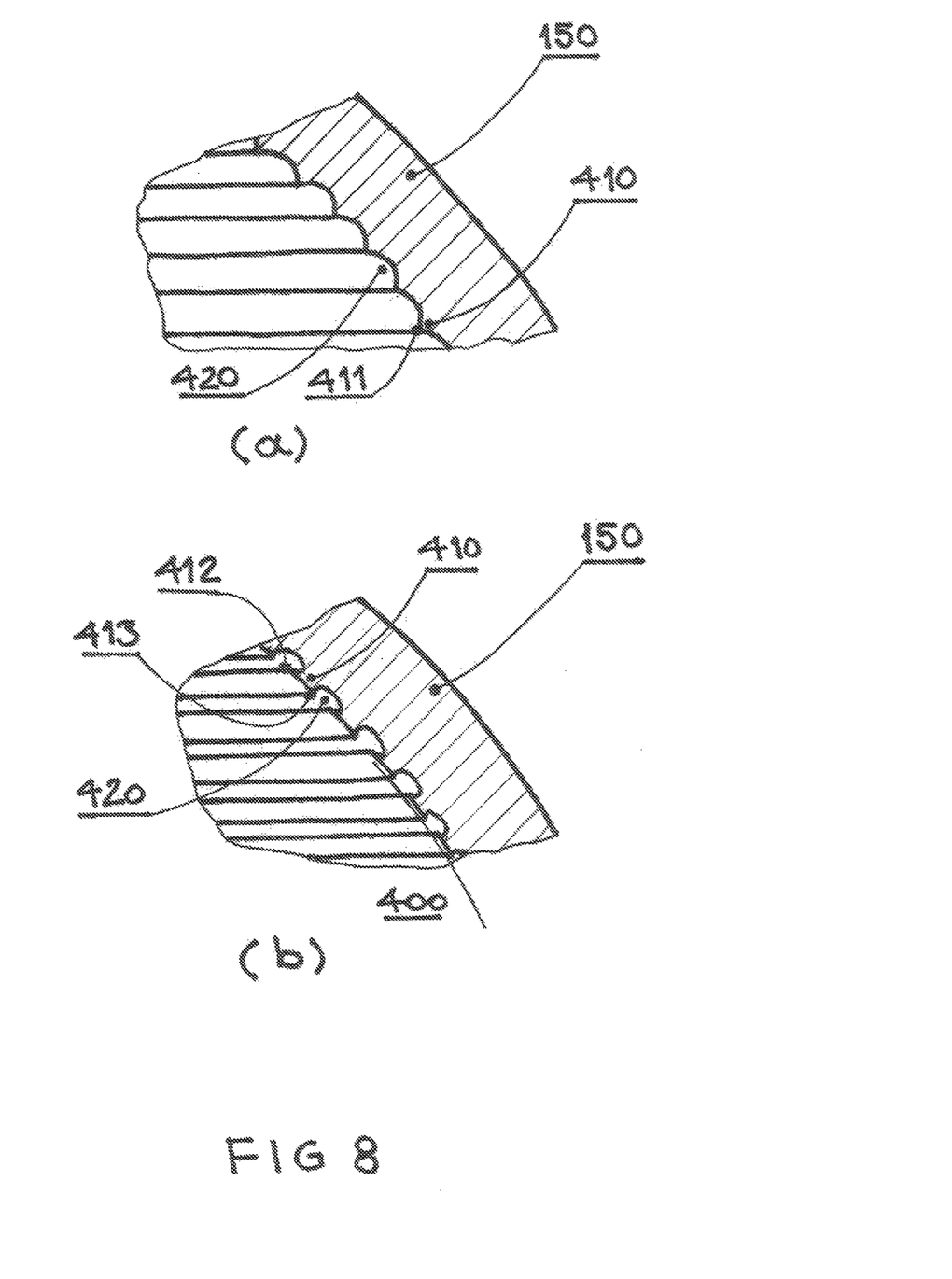
FIGS. 8a and 8b are cross sectional views of a portion of an insert showing surface roughness according to an embodiment of the invention.

According to embodiments of the present invention, a joint prosthesis may include metal-metal or ceramic-ceramic interactions at the band of contact 121 between the head 102 and the insert 150 within the cup 101. As noted above, efforts in reducing wear with metallic or ceramic components have included reducing roughness on the surfaces. According to accepted principles, both the head 102 and insert 150 may be highly polished to reduce roughness for improved wear at the band of contact 121. However, according to an embodiment of the invention, roughness is retained on the inner surface of the insert 150. The roughness retains lubricating fluids at the surface for improved interaction with the surface of the head 102. The desired roughness can be obtained during formation of the insert. Preferably, the desired spherical shape of the inner surface 151 of the insert 150 is obtained through a machining process of the metallic or ceramic material forming the insert. The typical machining process leaves small circular imperfections. The imperfections are illustrated in FIG. 8*a* which shows a cross sectional view of a portion of the insert. The imperfections 410 formed during machining include high points 411 with indentations 420 between respective high points. The indentations 420 are created by the machining step forming the insert. According to conventional wisdom, the high points 411 are removed through a polishing process to eliminate roughness. However, in this embodiment of the invention, the high points 411 are retained. The indentations 420 function to retain lubricating fluid within the band of contact 121 of the joint.

According to another embodiment of the invention, the inner surface 151 of a metallic insert 150 is further treated to create a desirable surface roughness. In this embodiment, illustrated in FIG. 8*b*, after the insert 150 is formed, a ball 400 is forced against the insert 150 under high pressure. The ball 400 has a spherical shape identical to that of the head 102. The insert is rigidly supported during this process to retain its shape. The pressure from the ball 400 acts upon the high points 411 to deform the contact surfaces of the imperfections 410. Specifically, the tip of the high point 411 is flattened creating two knobs 412, 413 thereon. The space between the knobs 412, 413 conforms to the shape of the ball, and, therefore, the head 102. The indentations 420 remain between the imperfections 410 to retain lubricating fluid.

According to another embodiment of the invention, imperfections are formed on the inner surface of a contact or articulating surface (e.g., an insert) through a sand blasting or similar process. This process creates random imperfections, rather than the circular ones formed in the foregoing process. Lubricating fluid remains in indentations between the imperfections. Thus, the imperfections in any embodiment can be ordered or random.

According to another embodiment of the invention, the convex component of the prosthesis and/or the second, harder material (e.g., within an insert of the concave component) may be hard-coated by coatings such as titanium nitride, chromium nitride, aluminum oxide, or can be a diamond or diamond-like to further reduce friction and wear.

There are many ways to approach the practical problem of designing more or less optimized shapes of different articulations. Simple analysis, based on known formulas for Herzian stresses, can be used to guide the design aiming to minimize the contact stresses. For a ball-and-socket joint, assuming no friction at the gliding surfaces, the result is straightforward, suggesting the optimum solution with the contact area centered at 45 degrees. Introducing friction, shifts the optimum angle downwards. And since the invention changes the mode of lubrication, hence the coefficient of friction, the problem of exactly solving for an optimum quickly becomes much more complex. Finite element method can be used to solve for solid stresses, and the optimum design can be sought by either parametric approach, or by min-max methods. Ultimately, fluid flow analysis could be incorporated into these models as well. To minimize the wear in the actual use, however, another, very serious escalation of complexity would have to be brought in—the mechanism of wear and the presumed regimen of use.

An alternative approach would be to start with analysis of the existing articulations, and then, by iteration, remove some material from a chosen side of the articulation, at the areas of maximum stress, aiming to minimize the peaks. For reduction of wear, a cost function should be created penalizing the locations prone to produce more wear in presumed physiological use, i.e. those which experience high relative motion when under load.

What is claimed is:

1. An articulating total joint prosthesis comprising
a convex (ball-type) member that articulates with a concave (cup-type) member, wherein
(a) the convex member has a first surface curvature, a portion of which defines a band of contact between the convex member and the concave member; and
(b) the concave member is made of a first material, has a second surface curvature different from the first surface curvature, has an annular recess and, positioned within the annular recess, an annular insert made of a second material that is harder than the first material, wherein the annular insert is centered on, and resides between 20 to 50 degrees from, an axis that passes through the center of the convex member and the center of the band of contact on the convex member.

2. The articulating total joint prosthesis of claim 1, wherein the first material is Ultra High Molecular Weight Polyethylene (UHMWPE).

3. The articulating total joint prosthesis of claim 2, wherein the second material is metal, ceramic, or a cross-linked UHMWPE.

4. The articulating total joint prosthesis of claim 1, wherein the convex member is metal or ceramic.

5. The articulating total joint prosthesis of claim 1, wherein the first surface curvature is spherical.

6. The articulating total joint prosthesis of claim 1, wherein the insert is positioned about a loading point of the joint.

7. The articulating total joint prosthesis of claim 1, wherein the prosthesis is configured to replace a hip joint.

8. The articulating total joint prosthesis of claim 1, wherein the prosthesis is configured to replace a knee joint.

9. The articulating total joint prosthesis of claim 1, wherein the prosthesis is configured to replace a spinal disk joint.

10. The articulating total joint prosthesis of claim 1, wherein the prosthesis is configured to replace a finger joint.

11. The articulating total joint prosthesis of claim 1, wherein the prosthesis is configured to replace an elbow joint.

12. The articulating total joint prosthesis of claim 1, wherein the prosthesis is configured to replace a wrist joint.

13. The articulating total joint prosthesis of claim 1, wherein the prosthesis is configured to replace an ankle joint.

14. The articulating total joint prosthesis of claim 1, wherein the inner surface of the insert includes a plurality of imperfections thereon and a plurality of indentations between the imperfections.

15. The articulating total joint prosthesis of claim 14, wherein each of the plurality of imperfections includes a plurality of knobs thereon.

16. The articulating total joint prosthesis of claim 1, wherein the surface of the convex member is hard-coated by one of titanium nitride, chromium nitride, aluminum oxide and a diamond-like coating.

17. The articulating total joint prosthesis of claim 1, wherein the inner surface of the insert is hard-coated by one of titanium nitride, chromium nitride, aluminum oxide and a diamond-like coating.

18. The articulating total joint prosthesis of claim 1, wherein the axis on which the annular insert is centered is offset from the axis of symmetry of the concave member.

* * * * *